United States Patent [19]

Liotta et al.

[11] 4,259,753

[45] Apr. 7, 1981

[54] FRAME SUPPORT FOR CARDIAC TISSUE VALVES

[76] Inventors: Domingo S. Liotta; Holga E. T. DeLiotta, both of Calle 3 de Febrero 2025, Buenos Aires, Argentina

[21] Appl. No.: 42,834

[22] Filed: May 29, 1979

[30] Foreign Application Priority Data

Mar. 16, 1979 [AR] Argentina .............................. 275852

[51] Int. Cl.³ ............................................... A61F 1/22
[52] U.S. Cl. ............................................................ 3/1.5
[58] Field of Search ................................................ 3/1.5

[56] References Cited

U.S. PATENT DOCUMENTS

| | | | |
|---|---|---|---|
| 3,548,418 | 12/1970 | Angell et al. | 3/1.5 |
| 3,570,014 | 3/1971 | Hancock | 3/1.5 |
| 3,744,062 | 7/1973 | Parsonnet | 3/1.5 |
| 3,755,823 | 9/1973 | Hancock | 3/1.5 |
| 4,035,849 | 7/1977 | Angell et al. | 3/1.5 |
| 4,079,468 | 3/1978 | Liotta et al. | 3/1.5 |

FOREIGN PATENT DOCUMENTS 1264472  2/1972  United Kingdom ................. 3/1.5

*Primary Examiner*—Clifford D. Crowder
*Attorney, Agent, or Firm*—Allison C. Collard; Thomas M. Galgano

[57] ABSTRACT

A frame support for a cardiac tissue valve is provided of the type including a hollow, substantially cylindrical body composed of a semi-flexible structure of a material such as polypropylene, covered by a medical grade fabric. The frame support defines two fully opposite ends or entrances, to the edge of which are sewed the aortic ring and the remaining portions of the resected sinuses of Valsalva including the commissural areas of the aortic wall of an animal valve, such as a porcine valve. The frame further includes an outer-widening or suture ring which defines a continuous ridge of the same fabric material. The frame has a wavy or scalloped proximal end and a distal end; the proximal end having a number of cusps corresponding to the number of commissures of the valve supported thereby. The maximum height of the cusps or crests of the wavy edge of the proximal end is in the range of a sixth of the maximum distance between both ends of the support frame; the distal end has supporting arms alternately spaced from each other by valleys (depths), the magnitude of which is three times the length of the mentioned cusps of the proximal end. The outer-widening or suture ring has a wavy conformation that follows the contour of the supporting arms and the valleys of the distal end. The width of the suture ring, measured parallel to the frame, from its distal point in the outer surface of the supporting arm to the depth of the valleys (FIG. 2-"h"), is of a magnitude similar to half the distance of the total height of the support frame.

3 Claims, 2 Drawing Figures

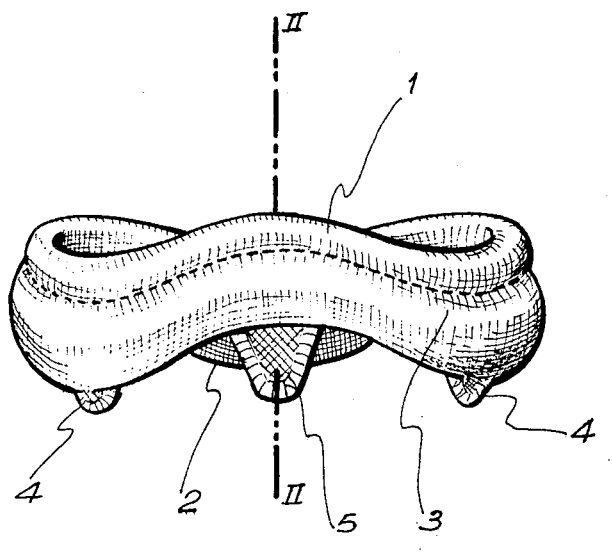
- FIG.1 -
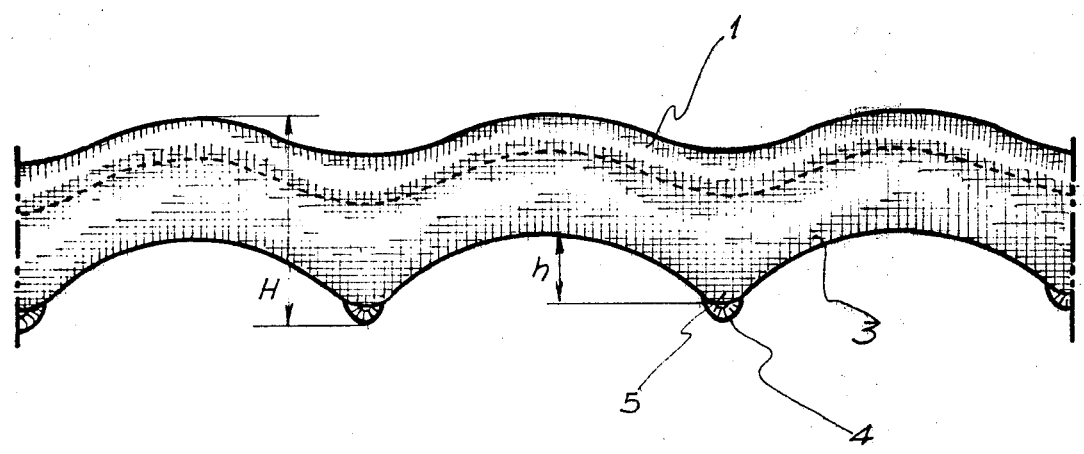
- FIG.2 -

FRAME SUPPORT FOR CARDIAC TISSUE VALVES

The present invention relates to a frame support for cardiac tissue valves. More particularly, it relates to a frame support for cardiac tissue valves of the type in which a frame and the valve form a bio-prosthesis, generally heterologous, which secured by suturing can replace an affected natural valve, either aortic or mitral.

In brief, the present invention relates to a frame support of the above-mentioned type, which includes a substantially cylindrical, hollow body having a height which is approximately half the diameter of its cavity. The frame support body is formed by a resistant and flexible structure of a synthetic material of acceptable medical grade, which is covered externally and internally with a textile and elastic material as, for example, jersey knit fabric with Dacron or similar yarn of acceptable medical grade. On the frame support body, a valve, generally heterologous and preferably porcine, is fixed by means of suture on its internal surface along its proximal and distal ends. On the outer surface of the frame body an outer-widening or suture ring is provided, whose purpose is to serve as means for the suture of the unit to the valvular annulus of the patient; this new support frame being characterized by the fact that its suture ring has a wavy conformation and the three supporting arms of the distal end which serve to support the commissures, are of a reduced height.

In this way, the suture ring follows the contour of the crests and the valleys or depths defined along the distal end; i.e., the supporting arms for the three commissures which provide these crests and valleys.

The fundamental objectives of the wavy shape of the suture ring are the following:

(a) The natural motion of the patient's valvular area during the cardiac cycle is transmitted to the bio-prosthesis. In fact, this occurs during the natural function of the heart.

In this manner, after mitral valve replacement the motion of the patient's mitral annulus during systole and during diastole are transmitted to the biological structures of the bio-prosthesis. In the same manner, after aortic valve replacement, the motion of the annulus and particularly of the aortic root are transmitted to the bio-prosthesis.

With respect to the preceding consideration, it must be stressed, that from the point of view of the function and durability of the valve, it is very important that the motion of the patient's valvular area be transmitted to the three commissures of the bio-prosthesis. This is what really occurs in the natural aortic valve, where the commissures follow the aortic wall motion during the cardiac cycle.

The wavy conformation of the suture ring permits one to precisely suture the commissures of the bio-prosthesis directly into the valvular annulus of the patient.

(b) Once the valve is totally incorporated into the cardiac tissue of the patient all possibilities of fracture or fatigue of the semi-rigid supporting material of the valve is avoided. This is in direct contrast to valves having long struts for commissure support, i.e., with struts which project outwardly for a relatively long distance from the suture ring (e.g., a "Hancock" type valve). In this case, if a fracture of a commissure support occurs, the closing function of the valve is destroyed, thereby necessitating an urgent valve replacement operation.

(c) As time passes, after the surgical implantation (approximately after one year) the invasion of the patient's connective tissue into the Dacron fabric of the suture ring further increases the incorporation into the patient's cardiac tissue of the entire anatomical structure of the implanted valve. In contrast thereto, the long struts of the Hancock type valves, freely and permanently, projected within the ventricular cavity or into the root of the aorta with the risk of fatigue or fracture of the struts.

The known bio-prosthesis support frames are derived from the heterologous aortic valve, typically porcine, based on the global conception of Hancock type valves, where the distal end of the cylindrical hollow body presents three arms for the support of the commissures, while the proximal end constitutes a circumferential ring lying in a plane perpendicular to the axis of support and wherein, in the same way, the suture ring surrounding the external surface follows a substantially parallel line with regard to the proximal end. Support frames which present an undulation in the proximal end and not in the suture ring are known as well (e.g., the "Ionescu" type).

Observations made in the cases where the above-mentioned prior art support frames have been used, have shown that, especially in the points where the commissures are sutured to the aforementioned support frames, the distances of the valvular annulus of the patient are important. This may mean a lack of concordance in the transmission of the mentioned cardiac movements, and it may also be a factor which provokes the rupture of the structural part of the support frame and therewith the loss of the functional capacity of the implanted valve, the only solution to which being an immediate replacement.

Such inconveniences have intensified investigations to solve these problems and have resulted in the support frame of the present invention, wherein a special proportionality condition for a wavy conformation for the suture ring has been incorporated as a new aspect, as well as a dimensional relationship between the diameter and the height of the support frame, which together with those conditions, eliminate the above-mentioned risks.

In effect, the suture ring of the present support frame has a wavy or scalloped profile, along the external surface of the hollow body which is practically similar to the wavy profile of the distal end. The distance between the distal portion of the support frames of the commissures and the valleys of the mentioned undulations or crests are not larger than half the height of the support frame. On the other hand, the height of this support frame is half its diameter.

With this conformation, the suture ring will coincide substantially with the disposition, which is wavy as well or arch-shaped, of each of the insertion bases of the aortic cusps of the patient, if an aortic replacement is practiced. On the other hand, if the mitral valve is replaced, when it is implanted in the patient's mitral ring, it does not produce any deformation to it.

Of fundamental importance is the reduced height of the commissural support as compared with the diameter of the same frame, which permits the referred leveling; in this manner, the danger of using frames with long struts disappears. The long struts put a burden on the semi-flexible structure of the frame with the possibility, as time passes, of material fatigue.

Other objects and features of the present invention will become apparent from the following detailed description, considered in connection with the accompanying drawing, which discloses a single embodiment of the invention. It is to be understood, however, that the drawing is designed for the purpose of illustration only, and not as a definition of the limits of the invention.

In the drawing, wherein similar reference characters denote similar elements throughout the several views:

FIG. 1 is a side view of a frame support for cardiac tissue valves, according to the present invention; and FIG. 2 is a side view of the frame support illustrated in FIG. 1, which was cut along line II—II thereof and uncoiled and flattened.

Referring now in detail to the drawing, as can be seen in FIG. 1 thereof, the frame support for the bio-prosthesis of the present invention is of the type which includes a substantially cylindrical, hollow body, which includes an internal frame made of a resistant plastic material which is of acceptable medical grade; such as medical grade polypropylene. This internal structure is covered externally and internally by a textile yarn material, of medical grade as well, of a knit such as "jersey". The outer surface of the internal frame is surrounded by a suture ring made out of the same textile material. The frame thus has a proximal or upper end 1, a lower or distal end 2 and a suture ring 3 lying therebetween on the outer surface of the body. In this example, the heterologous valve may be porcine, supported by the illustrated support frame and by the tri-valve formation, sutured by its aortic annulus to proximal end 1 which is wavy. The distal end 2 receives, by means of suture, the remaining portion of the resected sinuses of Valsalva. The three commissures of the porcine aortic valve are sutured to the inner surface of the supporting arms or struts 4.

In the drawing, it may be seen that the depth of the valleys of the waves, or crests or cusps of the distal end 2 of this frame support (or the heights of the crests thereof) are of a magnitude equivalent to the space occupied by the external surface of the suture ring, i.e., of similar height as indicated in FIG. 2 with reference to "h"; the total height of the frame support being represented by "H".

It is a condition of the invention that "h" may not exceed half the value of "H".

The point indicated by reference numeral 5 in FIG. 2, in the outer surface of the supporting arm, corresponds to the distal point of the sinuosities of the suture ring. At the same time, in the inner surface of the supporting arm it corresponds to the point where the valve commissures are sutured.

On the other hand, the waves of the proximal end 1 are frankly less pronounced and of a magnitude which may be equivalent at a maximum point to one-third of the mentioned height "h" of the suture ring.

In order to provide the explained shape conditions, the resistant semi-flexible structure or internal frame which is in the interior of the frame support has an upper ring with waves of reduced height conforming to the outer exterior of the proximal end, and opposite it has flexible columns such as thin wires molded in the same material, which surround the distal end 2.

In summary, in comparing this frame support with others that have long struts for the support of the commisures and a straight circular suture ring (e.g., Hancock, Angell-Shiley, Carpentier-Edwards, Ionescu-Shiley types), it has the following basic differences:

(1) The supporting arms for the sustaining of the three commissures are of a reduced length; and (2) The suture ring has a wavy or scalloped conformation that follows the contour of the distal end.

The three commissures are sutured directly into the valvular annulus of the patient. The functional motion of the annulus during the cardiac cycle is directly transmitted to the implanted commissures. The risks of fatigue or fracture associated with long commissural struts are avoided.

With this frame support it has been possible to mount a porcine valve after removing the sinuses of Valsalva including the aortic ridge. These anatomical structures (the sinuses of Valsalva and the aortic Ridge) were preserved in Liotta et al. U.S. Pat. No. 4,079,468.

While only a single embodiment of the present invention has been shown and described, it will be obvious that many modifications and changes may be made thereinunto, without departing from the spirit and scope of the invention.

What is claimed is:

1. A frame for tissue valves to be used in cardiac surgery of the type including a substantially cylindrical, hollow body fabricated from a semi-flexible, plastic material, a medical grade fabric cover which covers said body and which defines two fully open opposite ends, one of which is intended for suture to the valvular ring of an animal valve and the other end of which is intended for suture to the remaining portions of the resected sinuses of Valsalva including the commissural areas of the aortic wall of the animal valve, and a suture ring which surrounds the body and is fabricated from a medical fabric which may be sutured to the valvular annulus of a human heart, the improvement comprising:

said frame having a proximal and a distal end, both of which have a wavy configuration, said proximal end having a plurality of cusps corresponding to the number of commissures of the valve to be supported thereby, said cusps having a height equal to about one sixth of the maximum distance between said ends of said frame, said frame also including a plurality of short supporting arms joined to said distal end which are equidistantly spaced-apart by valleys, and which are alternately disposed relative to said cusps of said proximal end, said arms each having a total height which is about three times greater than the height of said cusps of said proximal end, and wherein said suture ring has a wavy configuration substantially conforming to the contour of said supporting arms and the valleys of said distal end and wherein said suture ring has alternately crests and valleys, on a distal edge thereof which crests, relative to the depths of said valleys thereof, have a height which is approximately no greater than half the total height of said frame.

2. The frame according to claim 1, wherein said cylindrical body is fabricated from medical polypropylene.

3. The frame according to claim 1, wherein said suture ring is made of the same fabric material which covers said body.

* * * * *